United States Patent
Sakata et al.

(10) Patent No.: US 11,571,376 B2
(45) Date of Patent: Feb. 7, 2023

(54) AQUEOUS ANTIMICROBIAL COMPOSITION

(71) Applicant: ARXADA AG, Visp (CH)

(72) Inventors: Kazuhiko Sakata, Chiba (JP); Mayumi Furukawa, Chiba (JP)

(73) Assignee: ARXADA AG, Visp (CH)

( * ) Notice: Subject to any disclaimer, the term of this patent is extended or adjusted under 35 U.S.C. 154(b) by 244 days.

(21) Appl. No.: 16/498,646

(22) PCT Filed: Mar. 28, 2017

(86) PCT No.: PCT/JP2017/012652
§ 371 (c)(1),
(2) Date: Sep. 27, 2019

(87) PCT Pub. No.: WO2018/179091
PCT Pub. Date: Oct. 4, 2018

(65) Prior Publication Data
US 2021/0106512 A1    Apr. 15, 2021

(51) Int. Cl.
| | | |
|---|---|---|
| A61K 8/00 | (2006.01) |
| A01N 25/00 | (2006.01) |
| A61Q 17/00 | (2006.01) |
| A61K 8/49 | (2006.01) |
| A01N 25/34 | (2006.01) |
| A01N 37/04 | (2006.01) |
| A01N 37/06 | (2006.01) |
| A01N 37/10 | (2006.01) |
| A01N 43/16 | (2006.01) |
| A61K 8/362 | (2006.01) |
| A61K 8/368 | (2006.01) |

(52) U.S. Cl.
CPC ............ *A61K 8/498* (2013.01); *A01N 25/34* (2013.01); *A01N 37/04* (2013.01); *A01N 37/06* (2013.01); *A01N 37/10* (2013.01); *A01N 43/16* (2013.01); *A61K 8/362* (2013.01); *A61K 8/368* (2013.01); *A61Q 17/005* (2013.01)

(58) Field of Classification Search
CPC combination set(s) only.
See application file for complete search history.

(56) References Cited

U.S. PATENT DOCUMENTS

| | | | |
|---|---|---|---|
| 5,141,803 A | 8/1992 | Pregozen | |
| 7,569,530 B1 * | 8/2009 | Pan | A01N 37/04 510/130 |
| 8,226,993 B2 * | 7/2012 | Jameson | A61P 31/04 424/725 |
| 2004/0091558 A1 * | 5/2004 | Lutz | A61Q 19/10 514/568 |
| 2011/0189347 A1 * | 8/2011 | Broz | A23K 20/20 426/531 |

FOREIGN PATENT DOCUMENTS

| | | | |
|---|---|---|---|
| JP | H02-061000 A | 3/1990 | |
| JP | H06-227940 A | 8/1994 | |
| JP | H06-508612 A | 9/1994 | |
| JP | H09-502974 A | 3/1997 | |
| JP | H10-109906 A | 4/1998 | |
| JP | H10-506393 A | 6/1998 | |
| JP | 2000-191521 A | 7/2000 | |
| JP | 2002-504115 A | 2/2002 | |
| JP | 2004-52942 A | 2/2004 | |
| JP | 2005-232014 A | 9/2005 | |
| JP | 2007-522132 A | 8/2007 | |
| JP | 2007-534701 A | 11/2007 | |
| JP | 2008-523066 A | 7/2008 | |
| JP | 2011-57687 A | 3/2011 | |
| JP | 2013-10694 A | 1/2013 | |
| JP | 2013-151447 A | 8/2013 | |
| WO | WO9221239 A1 | 12/1992 | |
| WO | WO9508267 A1 | 3/1995 | |
| WO | WO 9609761 A1 | 4/1996 | |
| WO | WO9855094 A1 | 12/1998 | |
| WO | WO2004/014416 A1 | 2/2004 | |
| WO | WO2005073359 A1 | 8/2005 | |
| WO | WO2005105070 A2 | 11/2005 | |
| WO | WO-2005105070 A2 * | 11/2005 | .............. A61L 2/18 |
| WO | WO2007044032 A2 | 4/2007 | |

OTHER PUBLICATIONS

PCT/JP2017/012652 Notice of International Preliminary Report on Patentability dated Oct. 1, 2019, 18 pages.

* cited by examiner

*Primary Examiner* — Sikarl A Witherspoon
(74) *Attorney, Agent, or Firm* — Dority & Manning, P.A.

(57) ABSTRACT

[Problem to be Solved]
An object of the present invention is to provide an aqueous antimicrobial composition which exhibits excellent antibacterial and antifungal activities even at a low concentration and has high safety, low skin irritation, and excellent long-term stability.
[Solution]
Aqueous antimicrobial compositions comprising two or more compounds selected from (a) benzoic acid or a salt thereof, (b) δ-gluconolactone, (c) ketonic acid or a salt thereof, and (d) sorbic acid or a salt thereof; and at least one or more dicarboxylic acid represented by General Formula (I) or a salt thereof.

7 Claims, No Drawings

AQUEOUS ANTIMICROBIAL COMPOSITION

CROSS REFERENCE TO RELATED APPLICATIONS

This application is the U.S. National Stage entry of International Application Number PCT/JP2017/012652 filed under the Patent Cooperation Treaty and having a filing date of Mar. 28, 2017, which is incorporated herein by reference.

TECHNICAL FIELD

The present invention relates to an aqueous antimicrobial composition impregnated in a wet wipe, for instance, used as a wipe for baby's bottom, a wipe for adult body or bottom, a wipe for hands and mouth, a sweat-absorbing sheet, or the like.

BACKGROUND ART

An aqueous antimicrobial composition, which is impregnated in a wet wipe, usually contains an active ingredient having an antiseptic and/or antifungal effect along water, alcohol and the like. Such a wet wipe is used directly in contact with the skin, and the active ingredient is therefore required to be highly safe, and have low skin irritation to a human body. Such properties are important, in particular, for a person having a low skin resistance such as an infant, and an aged person.

In recent years, warmers for keeping wet wipes used as wipers for baby's bottom at a suitable temperature have been used, and wet wipes may be stored in a higher temperature range (approximately in the range of 35-45 degrees Celsius) than room temperature. There is therefore need for long-term persistence of the antiseptic effect at such temperatures. Storage at such temperatures may cause discoloration of a chemical solution impregnated in the wet wipes. There is therefore also need for long-term stability of such a solution in a higher temperature range than mom temperature.

Conventionally, the following antibacterial compositions are disclosed.
Dimethyliminio
A. An aqueous composition for use in impregnation into nonwoven fabric wipe consisting of potassium sorbate, citric acid, disodium ethylenediamine tetraacetate, (a) polyhexamethylene biguanide hydrochloride or (b) a cation bioside, which is poly [oxyethylene (dimethyliminioy) ethylene (dimethyliminio) ethylene dichloride]; and water, wherein the pH of the composition is from about 3.5 to about 4.5. (Patent Document 1)
B. A sterilizer obtained by wetting a base fabric with a liquid containing a quaternary ammonium salt as a sterilizing and an N-coconut oil fatty acid acyl-L-arginine ethyl DL-pyrrolidone carboxylate. (Patent Document 2)
C. An antibacterial composition which comprises an antibacterially effective amounts of mixture comprising at least two of:
  (a) lemon glass oil;
  (b) cinnamaldehyde, cinnamide oil, cinnamomum cassia, cinnamon extract, cassia leaf oil, 3, 4-dihydroxycinnamic acid or a salt thereof, or a mixture thereof;
  (c) sorbic acid or a salt thereof;
  (d) erythorbic acid or a salt thereof;
  (e) benzoic acid or a salt thereof;
  (f) arabinogalactan, galactoarabinane, or mixtures thereof;
  (g) hexahydro-iso-alpha acid, tetrahydro-iso-alpha acid, or mixtures thereof;
  (h) *Achillea fragrantissima* oils, *Santolina fragrantissima* oils, Forssk oils, Lavender cotton oils; and
  (i) glucono-β-lactone. (Patent Document 3)
D. A composition for preventing proliferation of bacteria or fungi comprising an organic acid or a salt selected from the group consisting of: 2-(thiocyanomethylthio) benzothiazole, benzoic acid, sodium benzoate, p-hydroxybenzoic acid, sodium 2-hydroxybenzoate, dehydroacetic acid, sodium dehydroacetate, octanoic acid, nonanoic acid, formic acid, sorbic acid, potassium sorbate, acetic acid, oxalic acid, glycolic acid, citric acid, gluconic acid, malic acid, propionic acid, sodium propionate, lauric acid, undecylenic acid and sodium undecylenate. (Patent Document 4)
E. An antibacterial cleansing composition comprising:
  a. an antibacterial agent selected from the group consisting of triclosan, triclocarbine, octopix, PCMX, ZPT, natural essential oils and the like
  b. an anionic surfactant selected from the group consisting of sodium and aluminum alkyl sulfates and ether sulfates having chain lengths of predominantly 12 and 14 carbon atoms, olefin sulfates having chain lengths of predominantly 14-16 carbon atoms, paraffin sulfonates having an average chain length of 13 to 17 carbon atoms, and mixtures thereof;
  c. a proton donating agent selected from the group consisting of adipic acid, tartaric acid, citric acid, maleic acid, malic acid, succinic acid, glycolic acid, gluctaric acid, benzoic acid, malonic acid, salicylic acid, gluconic acid, polyacrylic acid, and salts thereof, and mixtures thereof; and
  d. water;
  wherein the antibacterial cleansing composition has a pH of 3.0 to 6.0. (Patent Document 5)
F. A water-soluble composition for impregnation into a fiber sheet, comprising a polyaminopropyl biguanide, or a mixture of a polyaminopropyl biguanide and a quaternary ammonium salt; sodium benzoate; citric acid, disodium ethylenediamine tetraacetate; a nonionic surfactant; and water; and wherein the pH of the chemical solution is 3.5 to 4.5. (Patent Document 6)
G. An antibacterial cleaning solution comprising a proton donating agent and an alkyl phosphate anionic surfactant, wherein the proton donating agent is selected from the group consisting of acetic acid, dehydroacetic acid, propionic acid, lactic acid, benzoic acid, p-hydroxybenzoic acid, ascorbic acid, isoascorbic acid, citric acid, sorbic acid, formic acid, phosphoric acid, malic acid, tartaric acid, adipic acid, succinic acid, caprilic acid, glutaric acid, salicylic acid, boric acid, monohalogenated acetic acid, dicarboxylic acid, fumaric acid, and combinations or mixtures thereof,
the alkyl phosphate anionic surfactant is selected from the group consisting of sodium mono lauryl phosphate, potassium mono lauryl phosphate, diethanolamine mono lauryl phosphate,triethanolamin mono lauryl phosphate, sodium mono coco phosphate, potassium mono coco phosphate, triethanolamine mono coco cphosphate, sodium mono capric phosphate, potassium mono capric phosphate, triethanolamine mono capric phosphate, and combinations thereof and mixtures thereof. (Patent Document 7)
H. A cosmetic characterized by comprising plant extract, and sulfurous acid or a salt thereof. (Patent Document 8)
I. A skin cosmetic characterized by comprising (A) two or more selected from γ-amino-β-hydroxybutyric acid and/or a salt thereof, N-acetylglucosamine, *Pyracantha fortuneana* extract, Geoscorea *Composita* extract, *Lonicera japonica* extract and *zanthoxylum* fruit extract; (B) one or more of sulfurous acid or sulfites selected from sulfurous acid, sulfite, hydrogen sulfurous acid, hydrogen sulfite, pyrosulfurous acid, and pyrosulfite; and (C) the extract of rhodominyrtus totrans. (Patent Document 9)

PRIOR ART DOCUMENTS

Patent Documents

Patent Document 1: JP H02-061000A
Patent document 2: JP 2000-191521A
Patent Document 3: JP 2011-57687A
Patent Document 4: JP H09-502974A
Patent Document 5: JP 2002-504115A
Patent Document 6: JP 2013-151447A
Patent Document 7: JP 2004-52942A
Patent Document 8: JP H06-227940A
Patent Document 9: JP 2013-10694A
Patent Document 10: JP 2005-232014A
Patent Document 11: JP 2011-057687A

SUMMARY OF INVENTION

Technical Problem

In this state of the art, the present invention provides an aqueous antimicrobial composition characterized by a new combination of active ingredients.

The present invention also provides an aqueous antimicrobial composition, which has excellent antiseptic and antifungal activities even at a low concentration as well as high safety, and low skin irritation, and which can maintain antiseptic and antifungal activities for a long period of time even when a temperature is kept higher than room temperature.

According to a preferable embodiment of the present invention, further provided is an aqueous antimicrobial composition which has good stability such as no discoloration for a long period of time.

Solution to Problem

The present invention provides the following aqueous antimicrobial compositions:
[1] An aqueous antimicrobial composition comprising:
two or more compounds selected from (a) benzoic acid or a salt thereof, (b) δ-gluconolactone, (c) ketonic acid or a salt thereof, and (d) sorbic acid or a salt thereof; and
(e) at least one or more of dicarboxylic acids represented by General Formula (I) or a salt thereof:

XOOC—R—COOX  (I)

wherein R is a bond, or a C1-C8 alkylene group, a C1-C8 alkenylene group or a C1-C8 alkynylene group, and X is hydrogen atom or alkali metal.
[2] The aqueous antimicrobial composition according to [1], which comprises (a) benzoic acid or a salt thereof, (b) δ-gluconolactone, (c) optionally ketonic acid or a salt thereof, (d) optionally sorbic acid or a salt thereof; and (e) at least one or more of dicarboxylic acids represented by General Formula (I) or a salt thereof.
[3] The aqueous antimicrobial composition according to [1] or [2], which comprises at least one of sulfurous acid or a salt thereof, pyrosulfurous acid or a salt thereof, thiosulfurous acid or a salt thereof, dithionous acid or a salt thereof, and phosphoric acid or a salt thereof.
[4] The aqueous antimicrobial composition according to any one of [1] to [3], wherein pH is 2.4-5.5.
[5] The aqueous antimicrobial composition according to any one of [1] to [4], wherein the dicarboxylic acid or the salt thereof is a malonic acid or a salt thereof.
[6] The aqueous antimicrobial composition according to any one of [1] to [5] comprising (a) 0.01-0.3 mass % of benzoic acid or a salt thereof, (b) 0 to 0.5 mass % of δ-gluconolactone, (c) 0-0.2 mass % of a ketone acid or a salt thereof, (d) 0-0.2 mass % of sorbic acid or a salt thereof, and (e) 0.01-0.3 mass % of at least one or more of dicarboxylic acids represented by General Formula (I) or salts thereof.
[7] A wet wipe comprising the aqueous antimicrobial composition according to any one of [1] to [6].
[8] The wet wipe according to [7], wherein the PH of the aqueous antimicrobial composition is 4.0-6.5.

The active ingredients having an antiseptic or antifungal effect selected for use in an aqueous antimicrobial composition of the present invention are all highly safe, and low irritative when applied to human skin. The active ingredients are all water-soluble, and a composition can be easily prepared with water as a solvent and does not cause precipitation or the like even after long-term storage. A dicarboxylic acid or a salt thereof, which is one of the active ingredients having these characteristics, is combined with other active ingredients to adjust the pH of the aqueous antimicrobial composition to about 5 or less, whereby the composition exhibits excellent antiseptic and antifungal activities, and even when a temperature thereof is kept equal to or higher than room temperature, antiseptic and antifungal activities are exhibited for a long period of time. According to a preferred embodiment, the pH is adjusted or a specific discoloration preventing agent is added, whereby the composition is not discolored for a long period of time, and storage stability is excellent even when a temperature thereof is kept equal to or higher than room temperature,

DESCRIPTION OF EMBODIMENTS

As mentioned above, an aqueous antimicrobial composition of the present invention comprises two or more compounds selected from (a) benzoic acid or a salt thereof, (b) δ-gluconolactone, (c) ketonic acid or a salt thereof, and (d) sorbic acid or a salt thereof; and (e) at least one or more of dicarboxylic acids represented by General Formula (I) or a salt thereof:

XOOC—R—COOX  (1)

wherein R is a bond, or a C1-C8 alkylene group, a C1-C8 alkenylene group or a C1-C8 alkynylene group, and X is hydrogen atom or alkali metal.

Salts of benzoic acid include sodium salt and potassium salt. Ketonic acids include dehydroacetic acid, pyruvic acid, oxaloacetic acid, α-keto acids such as α-ketoglutaric acid; β-keto acids such as acetoacetic acid, oxaloacetic acid, acetone dicarboxylic acid; and γ-keto acids such as levulinic acid, α-ketoglutaric acid and the like. α-ketonic acids such as dehydroacetic acid are preferred. Salts of the ketone acid include a sodium salt and a potassium salt. Salts of sorbic acid include a sodium salt and a potassium salt.

A dicarboxylic acid of General Formula (I) wherein R is a bond, is oxalic acid. Dicarboxylic acids represented by General Formula (1) wherein R is C1-C8 alkyl group includes malonic acid, succinic acid, glutaric acid, adipic acid, pimelic acid, suberic acid, azelaic acid, sebacic acid, malic acid, tartronic acid, tartaric acid and the like. Dicarboxylic acids represented by General Formula (I) wherein R is C1-C8 alkylene group include maleic acid, fumaric acid, glutaconic acid, isopropylidenesuccinic acid, citraconic acid, mesaconic acid, 2-pentenoic acid, allylmalonic acid, 2,4-hexadienoic acid and muconic acid. Dicarboxylic acids represented by General Formula (1) wherein R is C1-C8 alkynylene group include acetylene dicarboxylic acid and the like. In the present invention, from both sides of antiseptic effect and antifungal effect, at least one of malonic acid, fumaric acid, and maleic acid are preferable; at least one of maleic acid and fumaric acid are more preferable; and malonic acid is particularly preferable.

A aqueous antimicrobial composition of the present invention comprises preferably comprises a discoloration inhibitor in order to prevent the discoloration of the composition for a long period of time, even when the composition is kept at a temperature equal to or higher than room temperature. The discoloration inhibitor includes sulfurous acid or a salt thereof, pyrosulfurous acid or a salt thereof thiosulfurous acid or a salt thereof, dithionous acid or a salt thereof, and phosphoric acid or a salt thereof, and the composition preferably comprises at least one of these. Examples of salts of these acids include sodium salts and potassium salts. Specific examples of the discoloration inhibitors include sodium sulfite ($Na_2SO_3$), sodium hydrogen sulfite ($NaHSO_3$), sodium metabisulfite ($Na_2SO_5$), sodium thiosulfate ($Na_2S_2O_3$), sodium dithionite ($Na_2S_2O_4$), sodium dihydrogen phosphate ($NaH_2PO_4$), and disodium hydrogenphosphate ($Na_2HPO_4$).

In an aqueous antimicrobial composition of the present invention, pH is preferably 2.4-5.5, and more preferably 2.6 to 5.0, and most preferably 2.6-4.8. The pH of the composition can be put into a desired range, for example, by adjusting the content of the above-mentioned antiseptic and antifungal active ingredients.

According to a preferable embodiment of the present invention, an aqueous antimicrobial composition, from the viewpoints of preventing adsorption to a substrate, pH buffering effect, long-term stability such as long-term discoloration prevention, comprises (a) benzoic acid or a salt thereof; (b) δ-gluconolactone; (c) optionally a ketone acid or a salt thereof; (d) optionally sorbic acid or a salt thereof; (e) at least one or more of dicarboxylic acids represented by General Formula (I) or salts thereof, (f) optionally discoloration preventing agent comprising at least one selected from the group consisting of sulfurous acid or a salt thereof, pyrosulfurous acid or a salt thereof thiosulfurous acid or a salt thereof, dithionous acid or a salt thereof, and phosphoric acid or a salt thereof; wherein the pH of the composition is preferably 2.4 to 5.5, and more preferably 2.6 to 5.0.

According to a more preferable embodiment of the present invention, an aqueous antimicrobial composition comprises (a) benzoic acid or a salt thereof; (b) δ-gluconolactone; at least one of (c) a ketone acid or a salt thereof and (d) sorbic acid or a salt thereof, preferably a ketone acid or a salt thereof; (e) at least one of malonic acid, fumaric acid, maleic acid, glutamic acid and salts thereof, and preferably at least one of malonic acid, fumaric acid and salts thereof, and more preferably, malonic acid or a salt thereof; optionally at least one discoloration preventing agent selected from the group consisting of sulfurous acid or a salt thereof, pyrosulfurous acid or a salt thereof, thiosulfurous acid or a salt thereof, and dithionous acid or a salt thereof, preferably a sulfite or a salt thereof; wherein the pH of the composition is preferably 2.4 to 5.5, and more preferably 2.6 to 5.0.

The aqueous antimicrobial composition of the present invention basically comprises water as a solvent, because all the active ingredients are water-soluble, whereby it is possible to obtain an aqueous composition which does not generate a precipitate and has excellent storage stability for a long period of time, and the composition can be easily prepared.

Aqueous antimicrobial compositions according to the present invention may optionally comprise a hydrophilic solvent as a solubilization agent. The hydrophilic solvent includes ethanol, isopropanol, glycerin, ethyleneglycol, diethyleneglycol, polyethyleneglycol, propyleneglycol, dipropyleneglycol, hexylene glycol, butyleneglycol (1,3-butyleneglycol, 1,2-butyleneglycol, 1,4-butyleneglycol), propyleneglycol monocaprylate, and polyethyleneglycol caprylate.

Furthermore, aqueous antimicrobial compositions may optionally comprise hydrophilic surfactants as solubilization agents. Such hydrophilic surfactants include nonionic surfactants such as polyoxyethylene hydrogenated castor oil, polyoxyalkylene ether, polyoxyethylene alkyl ether, polyoxyethylene poly oxypropylene alkyl ether, polyoxyallyl ether, polyoxyalkylene amino ether, polyethyleneglycollauric acid diester, sorbitan laurate monoester, fatty acid ester of glycerin, and sorbitan fatty acid ester, anionic surfactants such as sodium fatty acid, alkylsulfate, polyoxyethylene sulfate, alkylbenzenesufonate, α-olefinsulfonate, alkylphosphate; and amphoteric surfactants such as alkyldimethylaminoexide, alkylcarboxybetaine, alkylsulfobetaine, amide amino acid salt, lauryldimethylaminoacetate betaine, coconut oil fatty acid amide propyl betaine.

According to an embodiment of the present invention, aqueous antimicrobial compositions may, in addition to the above-mentioned ingredients (a)-(e), comprise one or more other sterilizing/antimicrobial agents. Examples of such other sterilization/antimicrobial agents are as follows.

Isothiazolin compounds: e.g., 5-chloro-2-methyl-4-isothiazolin-3-one, 2-methyl-4-isothiazolin-3-one, and 2-methyl-4,5-trimethylene-4-isothiazolin-3-one;

Cationic compounds: e.g., cetylpyridinium chloride, benzalkonium chloride; quaternary ammonium salt such as didecyldimethylammonium chloride (DDAC), didecylmethylpolyoxyethyleneammonium propionate, didecylmethylammonium carbonate, benzethonium chloride; imidazole derivatives such as 1,10-di(3-decyl-2-methylimidazolium) decane dichloride;

Guanidine compounds: e.g., chlorhexidine, or hydrochloride, gluconate or acetate thereof, polyhexamethylene biguanide (PHMB), polyhexamethylene guanidine (PHMG);

Bromine compounds: e.g., 2,2-dibromo-3-nitrilopropionamide, 2-bromo-2-nitropropane-1,3-diol, 2,2-dibromo-2-nitromethanol, 1,4-bis(bromoacetoxy)-2-butene, 1,2-bis(bromoacetoxy)ethane, 1,2-dibromo-2,4-dicyanobutane;

Iodine compounds: e.g., 3-iodo-2-propynyl-N-butyl carbamate, diiodomethyl-p-tolylsulfone, 4-chlorophenyl-3-iodopropargylformal, 3-ethoxycarbonyloxy-1-bromo-1,2-diiodo-1-propene, and 2,3,3-triiodoallylalcohol;

Pyridine compounds: e.g., zinc pyrithione (zinc pyrithione ZPT), copper pyrithione, sodium pyrithione, methyl sulfonyl tetrachloro pyridine; and Others: salicylic acid and salicylic acid salts, propionic acid and salts thereof, silver compound, trichlorohydroxy diphenyl ether (triclosan), p-oxybenzoate and sodium salts thereof (methyl paraben, propyl paraben, butyl paraben, ethyl paraben, isopropyl paraben, benzyl paraben), phenoxy ethanol, phenol, sodium lauryldiaminoethylglycine, isopropylmethylphenol, bisaminopropyldodecylamine, o-phenylphenol, sodium o-phenylphenol, cresol, 1,3-dimethylol-5,5-dimethylhydantoin, alkylisoquinolinium bromide, thianthol, thymol, trichlorocarvanide, p-chlorphenol, halocarban, hinokithiol, benzylalcohol, 2-bromo-2-nitropropane-1,3-diol (BRONOPOL), methyldibromonitrile, glutaronitrile(1,2-dibromo-2,4-dicyanobutane), 5-bromo-5-nitro-1,3-dioxane), chlorphenesin, and phenoxyisopropanol.

An aqueous antimicrobial composition according to the present invention may also comprise a complex composed of antibacterial and antifungal agents included in a clathrate compound such as cyclodextrin (in α-, β-, or γ-form) and dispersed in water.

In the aqueous antimicrobial composition of the present invention, the content of each ingredient is not particularly limited, but the content of each active ingredient can be reduced because a combination of the above ingredients (a) to (e) exhibits a high antiseptic and antifungal effect. From this perspective, the total content of the active ingredients of (a) to (e) and other sterilization/the antibacterial agents can be 1 mass % or less, preferably 0.3 to 0.8 mass %.

According to a preferable embodiment of the present invention, an aqueous antibacterial composition comprises 0.01-0.5 mass %, preferably 0.05-0.4 mass %, and more preferably 0.07-0.3 mass % of benzoic acid or a salt thereof. The composition also comprises 0-0.5 mass %, preferably 0.01-0.3 mass %, more preferably 0.02-0.1 mass % of δ-gluconolactone. Further, the composition comprises 0-0.2 mass %, preferably 0-0.1 mass % of a ketone acid or a salt thereof. Further, the composition comprises 0-0.2, preferably 0-0.1 mass % of sorbic acid or a salt thereof. The composition comprises 0.01-0.4 mass %, preferably 0.07-0.3 mass % of at least one of dicarboxylic acids represented by Formula (I) or salts thereof. The composition comprises 0-1.0 mass %, more preferably 0.01-0.3 mass %, and more preferably 0.02 to 0.2 mass % of a discoloration inhibitor. The composition may comprise 0-1 mass % of a hydrophilic solvent, and 0-0.5 mass % of a hydrophilic amphoteric surfactant. The composition may comprise 0.2 mass % or less, preferably 0.1 mass % or less of other sterilization/antibacterial agents. The composition also may comprise 0.1 mass % or less of the other additive components.

According to a preferred embodiment of the present invention, (a) 0.01-0.5 mass % of benzoic acid or a salt thereof, (b) 0-0.5 mass % of delta-gluconolactone, (c) 0-0.2 mass % of a ketone acid or a salt thereof, (d) 0-0.2 mass % sorbic acid or a salt thereof; and (e) 0.01-0.4 mass % of at least one or more of dicarboxylic acids represented by the formula (I) or salts thereof, and 0-1.0 mass % of a discoloration inhibitor. According to a more preferable embodiment of the present invention, (a) 0.05-0.4 mass %, more preferably 0.07-0.3 mass % of benzoic acid or a salt thereof, (b) 0.01-0.3 mass %, more preferably 0.02-0.1 mass % of δ-gluconolactone, (c) 0-0.1 mass % of a ketone acid or a salt thereof, (d) 0-0.1 mass % sorbic acid or a salt thereof; and (e) 0.07-0.3 mass % of at least one selected from the group consisting of a dicarboxylic acid represented by Formula (or a salt thereof, preferably at least one selected from fumaric acid, malonic acid and salts thereof, more preferably malonic acid or a salt thereof; and 0.01 to 0.3 mass %, more preferably 0.02 to 0.2 mass % of a discoloration inhibitor.

An aqueous antimicrobial compositions of the present invention may be typically impregnated into a base material to a wet wipe. The base material includes nonwoven fabrics composed of natural or synthetic fibers, paper, gauze, towels, and clothes. More specifically, the base material may be preferably spunlace nonwoven fabrics containing one or more fibers selected from a hydrophilic fiber such as rayon or pulp and synthetic fibers such as polyester, polyethylene, and polypropylene and thereby having a strong wet strength. These base materials may be any of water-disintegrable, poorly water-disintegrable, and non-water-disintegrable materials.

The size of sheets used as the base materials is appropriately determined depending on a region to be applied or a container or package for containing the sheets.

The amount of aqueous antimicrobial compositions impregnated in base materials can be appropriately determined. The amount is preferably 150-500 parts by weight and more preferably 200-400 parts by weight relative to 100 parts by weight of a base material. At less that 150 parts by weight, a sufficient wiping ability may not be expected, and wet wipes are prone to be dried. At more than 500 parts by weight, it becomes difficult to maintain them in wet wipes and skin becomes too wet when they were used to wipe skin.

When a base material is impregnated with an aqueous antimicrobial composition, in many cases, the pH of the aqueous antimicrobial composition increases, which might vary dependent on the base material, though. In an aqueous antimicrobial composition of the present invention, the PH is preferably 2.4-5.5, and more preferably 2.6-5.0 in this regard. The pH of an aqueous antibacterial composition after being impregnated into a base material, may be in the range of 2.6-6.5, but is typically 4.0 to 6.5.

EXAMPLES

Examples of the present invention are described below, but the present invention is not limited.

Examples 1-15 and Comparative Examples 1-3

Each ingredient shown in Table 1 below is dissolved in sterile water to prepare each composition.

TABLE 1-1

| | Composition No. | | | | | | | |
|---|---|---|---|---|---|---|---|---|
| Ingredients | 1 | 2 | 3 | 4 | 5 | 6 | 7 | 8 |
| Propylene glycol (PG) | 0.35 | 0.35 | 0.35 | 0.35 | 0.35 | 0.4 | 0.4 | 0.4 |
| PEG60 Hydrogenated castor Oil CH60 | 0.01 | 0.01 | 0.01 | 0.01 | 0.01 | 0.01 | 0.01 | 0.01 |
| Na Dehydroacetate | | | | | | 0.05 | 0.05 | 0.075 |
| Sodium benzoate | 0.09 | 0.09 | 0.09 | 0.09 | 0.09 | 0.275 | 0.275 | 0.25 |
| δ-gluconolactone | 0.26 | 0.26 | 0.26 | 0.26 | 0.26 | 0.025 | 0.025 | 0.025 |
| Malonic acid | 0.1 | | | 0.1 | | 0.15 | | |
| Maleic acid | | 0.1 | | | | | 0.15 | |
| Fumaric acid | | | 0.1 | | 0.1 | | | 0.15 |
| 50% of Hyamine 3500J [*1] | 0.01 | 0.01 | 0.01 | 0.01 | 0.01 | | | |

TABLE 1-1-continued

| Ingredients | \multicolumn{8}{c}{Composition No.} | | | | | | | |
|---|---|---|---|---|---|---|---|---|
| | 1 | 2 | 3 | 4 | 5 | 6 | 7 | 8 |
| EDTA 2Na | 0.05 | 0.05 | 0.05 | 0.05 | 0.05 | | | |
| Sodium sulfite | 0.05 | 0.05 | 0.05 | | | 0.05 | 0.05 | 0.05 |
| Sodium hydrogen sulfite | | | | 0.05 | 0.05 | | | |
| Total | 0.92 | 0.92 | 0.92 | 0.92 | 0.92 | 0.96 | 0.96 | 0.96 |
| pH[*3] | 3.3 | 2.9 | 3.3 | 3.2 | 2.8 | 4.2 | 4.5 | 4.0 |

TABLE 1-2

| Ingredients | Composition No. | | | | | | |
|---|---|---|---|---|---|---|---|
| | 9 | 10 | 11 | 12 | 13 | 14 | 15 |
| Propylene glycol (PG) | 0.4 | 0.4 | 0.35 | 0.35 | 0.35 | 0.4 | 0.4 |
| Polyoxy hydrogeneted castor oil CH60 | 0.01 | 0.01 | 0.01 | 0.01 | 0.01 | 0.01 | 0.01 |
| Na Dehydroacetate | 0.03 | 0.045 | | | | 0.045 | 0.045 |
| Sodium benzoate | 0.165 | 0.15 | 0.09 | 0.09 | 0.09 | 0.165 | 0.165 |
| δ-gluconolactone | 0.015 | 0.015 | 0.26 | 0.26 | 0.26 | | |
| Glutaric acid | | | 0.1 | | | | |
| Malonic acid | 0.09 | | | | | 0.09 | |
| Maleic acid | | | | 0.1 | | | |
| Fumaric acid | | 0.09 | | | 0.1 | | 0.09 |
| Citric acid | | | | | | | |
| 50% of Hyamine 3500J [*1] | | | 0.01 | 0.01 | 0.01 | | |
| Cosmocil CQ[*3] | | | | | | | |
| EDTA 2Na | | | 0.05 | 0.05 | 0.05 | 0.05 | |
| Sodium sulfite | 0.05 | 0.05 | | | | 0.05 | 0.05 |
| Total | 0.76 | 0.76 | 0.87 | 0.87 | 0.87 | 0.76 | 0.76 |
| pH[*3] | 4.3 | 4.1 | 3.8 | 2.7 | 3.1 | 4.5 | 4.5 |

TABLE 1-2

| Ingredients | Comparative Example 1 | Comparative Example 1 | Comparative Example 1 |
|---|---|---|---|
| Propylene glycol (PG) | 0.5 | 0.5 | 0.5 |
| Polyoxy hydrogeneted castor oil CH60 | 0.01 | 0.01 | 0.01 |
| Na Dehydroacetate | 0.2 | 0.3 | |
| Sodium benzoate | 0.2 | | 0.3 |
| δ-gluconolactone | | | |
| Citric acid | | 0.05 | 0.05 |
| 50% of Hyamine 3500J [*1] | | | |
| Cosmocil CQ[*2] | | 0.1 | 0.1 |
| EDTA 2Na | 0.05 | 0.05 | 0.05 |
| Sodium sulfite | | | |
| Total | 0.96 | 1.01 | 1.01 |
| pH[*3] | 5.4 | 5.3 | 4.9 |

[*1] the numerial values other than pH values in the table show weight % based on the total weight of each composition.
[*2] active ingredient: 50% of benzalkonium chloride, Lonza.
[*3] active ingredient: 20% of polyhexamethylene biguanide, Lonza.

<Method of Evaluation>

Evaluation of the wet wipes for antibacterial and antifungal properties and discoloration preventing effects was conducted in accordance with the methods below.

(Test for Antiseptic and Antifungal Effects)
(1) Test Microbes
  *Escherichia coli* NBRC 3972 (*E. coli*)
  *Pseudomonas aeruginosa* NBRC 13275 (*P. aeruginosa*)
  *Staphylococcus aureus* subsp. *aureus* NBRC 13276 (*S. aureus*)
  *Aspergillus brasiliensis* NBRC 9455 (*A. brasiliensis*)
  *Cladosporium cladosprioides* NBRC 6348 (*Cladosporium*)

(2) Media for Tests
NA medium: a nutrient agar [Eiken Chemical Co., Ltd.]
PDA medium: a potato dextrose agar [Eiken Chemical Co., Ltd.]:
SCDLP medium: Soybean-Casein Digest Broth with Lecithin& Polysorbate80 [Nippon Seiyaku Co., Ltd.]
GPLP medium: Glucose Peptone Broth with Lecithin&Polysorbate80 [Nippon Pharmaceutical Co., Ltd.]:
Neutralizer: D/E Neutralizing Broth [DIFCO]:
(3) Preparation of Microbial Suspensions
  a) *E. coli, P. aeruginosa*, and *S. aureus* were cultured in the NA for 24 hours, at 35° C.±1° C. The cells of the obtained test microbes were then suspended into a sterilization phosphate buffered saline. Suspensions at a cell density of 1-5×10$^8$ cells/ml were prepared as test microbe suspensions.
  b) *Aspergillus brasiliensis* (*A. brasiliensis*) and *Cladosporium* cladosprioides (*Cladosporium*) were cultured in the PDA medium for 10 days at 27° C.±1° C. The obtained spores of the test microbes were then suspended in a physiological saline containing 0.005% of Polysorbate 80. Suspensions at a spore density of about 5×10$^6$-1×10$^7$ spores/ml were prepared as fungal suspensions.
(4) Preparation of Samples
  For this evaluation, a nonwoven fabric made of a blend of rayon/polyester was used as a base cloth. 280 parts by weight of each of the aqueous antimicrobial compositions shown in Table 1 relative to 100 parts by weight of the nonwoven fabric was impregnated in the nonwoven fabric. The obtained test wet wipes were each stored for 4 weeks at 50° C. After storage for 4 weeks, the wet wipes containing the aqueous antimicrobial compositions were squeezed and the squeezed fluids were collected. 20 ml aliquots of the squeezed fluids were dispensed into sterilized containers. Sterilized physiological saline was used as a control sample.

(5) Test Procedure

The fluid squeezed from each of the wet wipes was inoculated with 0.2 ml (1% by weight) of each test microbe suspension and incubated in an incubator at 25° C. For bacteria counts, after the incubation for 6, 24, and 48 hours, 1 ml of each sample was collected and transferred into 9 ml of the neutralizer D/E Neutralizing Broth. For fungal counts, after the incubation for 48 hours, 72 hours, and 7 days, 1 ml of each sample was collected and transferred into 9 ml of the neutralizer D/E Neutralizing Broth. The number of cells in each of the neutralizer D/E Neutralizing Broth fluids was measured. The number of bacteria was measured by culturing the cells for 48 hours at 37° C. in the SCDLP petriplate method. The number of fungi was measured by culturing the cells for 72 hours at 28° C. in the GPLP petriplate method.

The fluids were considered to have an antimicrobial effect when the number of cells is less than $10^1$ cells/ml for bacteria and less than $10^2$ spores/ml for fungi.

(Tests for Discoloration Preventing Effects)

In the same manner as described above, the composition of each Example and Comparative Example was impregnated into nonwoven fabric, the nonwoven fabric impregnated with each of the compositions was stored at 50'C for 4 weeks, then the impregnated liquid was squeezed from each of the wet wipes and collected. The state of the squeezed fluids was observed by visual observation, transparent and colorless ones were evaluated as ○; colored or yellowed fluids, or fluids with precipitates are evaluated as x.

The test results of the compositions of Examples 1-13 and Comparative Examples 1-3 regarding antiseptic and antifungal effects and discoloration preventing effective are summarized in Table 2 below.

TABLE 2

| Bacterial Test | 6 H | | 24 H | | 48 H | | Preservative Effect | Squeezed fluid from 50° C. 4 W stored wet wipe |
| --- | --- | --- | --- | --- | --- | --- | --- | --- |
| | N1 | N2 | N1 | N2 | N1 | N2 | | |
| Ex. 1 | 8.0E+02 | 6.0E+02 | <10 | <10 | <10 | <10 | Effective | No yellowing ○ |
| Ex. 2 | <10 | <10 | <10 | <10 | <10 | <10 | Effective | No yellowing ○ |
| Ex. 3 | 1.0E+01 | <10 | <10 | <10 | <10 | <10 | Effective | No yellowing ○ |
| Ex. 4 | 6.0E+02 | 4.0E+02 | <10 | <10 | <10 | <10 | Effective | No yellowing ○ |
| Ex. 5 | 1.0E+01 | 1.0E+01 | <10 | <10 | <10 | <10 | Effective | No yellowing ○ |
| Ex. 6 | 1.0E+04 | 9.0E+03 | <10 | <10 | <10 | <10 | Effective | No yellowing ○ |
| Ex. 7 | 1.5E+05 | 1.4E+05 | 4.0E+01 | 2.0E+01 | <10 | <10 | Effective | No yellowing ○ |
| Ex. 8 | 4.0E+04 | 5.0E+04 | <10 | <10 | <10 | <10 | Effective | No yellowing ○ |
| Ex. 9 | 1.5E+05 | 1.1E+05 | 9.0E+01 | 1.7E+02 | <10 | <10 | Effective | No yellowing ○ |
| Ex. 10 | 1.7E+05 | 1.6E+05 | 2.0E+03 | 4.0E+03 | <10 | <10 | Effective | No yellowing ○ |
| Ex. 11 | 4.0E+03 | 3.0E+03 | <10 | <10 | <10 | <10 | Effective | Yellowing X |
| Ex. 12 | <10 | <10 | <10 | <10 | <10 | <10 | Effective | Yellowing X |
| Ex. 13 | 2.0E+01 | <10 | <10 | <10 | <10 | <10 | Effective | Yellowing X |
| Ex. 14 | 1.2E+05 | 1.8E+05 | 2.0E+02 | 3.0E+02 | <10 | <10 | Effective | No yellowing ○ |
| Ex. 15 | 1.9E+05 | 1.7E+05 | 1.0E+02 | 4.0E+02 | <10 | <10 | Effective | No yellowing ○ |
| Com. Ex. 1 | 2.0E+04 | 6.0E+04 | 4.0E+03 | 4.0E+03 | 2.0E+02 | 8.0E+01 | Non-effective | Yellowing X |
| Com. Ex. 2 | 2.5E+03 | 3.5E+03 | 2.0E+02 | 4.0E+02 | 1.0E+02 | 6.0E+01 | Non-effective | Yellowing X |
| Com. Ex. 3 | 5.0E+05 | 8.0E+05 | 2.0E+03 | 2.5E+03 | 2.0E+02 | 1.5E+02 | Non-effective | No yellowing ○ |
| Blank | 1.30E+06 | | 1.70E+06 | | 2.50E+06 | | Non-effective | — |

| Fungal Test | 48 H | | 72 H | | After 7 days | | Preservative Efect t | Squeezed fluid from 50° C. 4 W stored wet wipe |
| --- | --- | --- | --- | --- | --- | --- | --- | --- |
| | N1 | N2 | N1 | N2 | N1 | N2 | | |
| Ex. 1 | 2.0E+02 | 1.0E+02 | 1.0E+02 | 1.0E+02 | 8.0E+01 | 3.0E+01 | Effective | No yellowing ○ |
| Ex. 2 | 3.0E+01 | 2.0E+01 | 1.0E+01 | <10 | <10 | <10 | Effective | No yellowing ○ |
| Ex. 3 | 2.0E+02 | 3.0E+02 | 1.0E+01 | <10 | 1.0E+01 | <10 | Effective | No yellowing ○ |
| Ex. 4 | 2.0E+02 | 1.0E+02 | 1.0E+02 | 4.0E+01 | 2.0E+01 | <10 | Effective | No yellowing ○ |
| Ex. 5 | 4.0E+02 | 4.0E+02 | 2.0E+01 | <10 | 1.0E+01 | <10 | Effective | No yellowing ○ |
| Ex. 6 | <10 | <10 | <10 | <10 | <10 | <10 | Effective | No yellowing ○ |
| Ex. 7 | 2.0E+03 | 1.0E+03 | 3.0E+03 | 2.0E+03 | 2.0E+01 | 3.0E+01 | Effective | No yellowing ○ |
| Ex. 8 | 4.2E+02 | 1.0E+02 | 7.0E+01 | 7.0E+01 | <10 | <10 | Effective | No yellowing ○ |
| Ex. 9 | <10 | <10 | <10 | <10 | <10 | <10 | Effective | No yellowing ○ |
| Ex. 10 | 3.0E+02 | 3.0E+02 | 8.0E+01 | 6.0E+01 | 2.0E+01 | <10 | Effective | No yellowing ○ |
| Ex. 11 | 4.0E+02 | 3.0E+02 | 6.0E+01 | 4.0E+01 | 1.0E+01 | 2.0E+01 | Effective | Yellowing X |
| Ex. 12 | 4.0E+01 | 3.0E+01 | 1.0E+01 | 2.0E+01 | <10 | <10 | Effective | Yellowing X |
| Ex. 13 | 2.0E+02 | 4.0E+02 | 1.0E+01 | 1.0E+01 | 4.0E+01 | 2.0E+01 | Effective | Yellowing X |
| Ex. 14 | 4.0E+01 | 2.0E+01 | <10 | <10 | <10 | <10 | Effective | No yellowing ○ |
| Ex. 15 | 2.0E+02 | 4.0E+02 | <10 | 4.0E+01 | 1.0E+01 | 3.0E+01 | Effective | No yellowing ○ |
| Com. Ex. 1 | 2.0E+03 | 1.0E+04 | — | — | 6.0E+03 | 4.0E+03 | Non-effective | Yellowing X |
| Com. Ex. 2 | 1.0E+03 | 2.0E+03 | — | — | 8.0E+02 | 2.0E+03 | Non-effective | Yellowing X |
| Com. Ex. 3 | 4.0E+04 | 4.0E+04 | — | — | 2.0E+04 | 6.0E+04 | Non-effective | No yellowing ○ |
| Blank | 6.00E+04 | | 4.0E+04 | | 3.00E+04 | | Non-effective | — |

As shown above, the aqueous antimicrobial compositions of Examples 1-13 have sufficient antiseptic and antifungal effects, and discoloration inhibiting effects.

The invention claimed is:

1. An aqueous antimicrobial composition comprising:
   (a) benzoic acid or a salt thereof,
   (b) δ-gluconolactone,
   (c) optionally a ketonic acid or a salt thereof,
   (d) optionally sorbic acid or a salt thereof; and (e) at least one dicarboxylic acids represented by General Formula (I) or a salt thereof:

XOOC—R—COOX     (I)

wherein R represents a bond; or a C1-C8 alkylene group, a C1-C8 alkenylene group or a C1-C8 alkynylene group; and X represents a hydrogen atom or an alkali metal.

2. The aqueous antimicrobial composition according to claim 1 comprising at least one of sulfurous acid or a salt thereof, pyrosulfurous acid or a salt thereof, thiosulfurous acid or a salt thereof, dithionous acid or a salt thereof, and phosphoric acid or a salt thereof.

3. The aqueous antimicrobial composition according to claim 1, wherein the pH is 2.4 to 5.5.

4. The aqueous antimicrobial composition according to claim 1, wherein the dicarboxylic acid or the salt thereof is a malonic acid or a salt thereof.

5. The aqueous antimicrobial composition according to claim 1, comprising (a) 0.01-0.3 mass % of benzoic acid or a salt thereof, (b) 0-0.5 mass % of β-gluconolactone, (c) 0-0.2 mass % of a ketonic acid or a salt thereof, (d) 0-0.2 mass % of sorbic acid or a salt thereof, and (e) 0.01-0.3 mass % of at least one or more of dicarboxylic acids represented by General Formula (I) or salts thereof.

6. A wet wipe comprising the aqueous antimicrobial composition according to claim 1.

7. The wet wipe according to claim 6, wherein the aqueous antimicrobial composition has a pH of 4.0 to 6.5.

* * * * *